United States Patent [19]

Darby

[11] Plant 4,271

[45] Jun. 27, 1978

[54] HIBISCUS PLANT NAMED LADY BALTIMORE

[76] Inventor: Robert H. Darby, 4813 Harvard Rd., College Park, Md. 20740

[21] Appl. No.: 835,828

[22] Filed: Sep. 22, 1977

[51] Int. Cl.[2] ..... A01H 5/00

[52] U.S. Cl. ..... Plt./68

[58] Field of Search ..... Plt./68

*Primary Examiner*—Robert E. Bagwill

[57] ABSTRACT

The present invention relates to a new and distinct Hibiscus plant cultivar named "Lady Baltimore," resulting from a definite effort, over a period of time, to produce by hybridization and selection a pink-and-red bicolor of elegant form and substance, a plant of great landscape value blooming profusely from midsummer to frost, a plant as excellent in its way as the brilliant red Hibiscus "Lord Baltimore."

2 Drawing Figures

BACKGROUND OF THE NEW PLANT

It should be noted that most hibiscus hydridizers, including even some of the more recent ones, have emphasized bigness over all else: the plants are coarse, the foliage is coarse, and the flowers are coarse. Others have striven for some refinement of plant and leaf, and so have tolerated smaller flowers, but have insisted on flowers that open out flat, which is not necessarily the most attractive form.

The objective of this program was primarily to develop a plant with the following characteristics:

(a) Decorative and unobtrusive foliage, sparse enough to permit close underplanting with annuals or perennials.
(b) A flower, preferably a pink-and-red bicolor, of real elegance rather than mere size.
(c) A plant of medium size, of good form and habit, and of good landscaping quality.

The hybridization was conducted over a period of years using as seed parent "Lord Baltimore," which first bloomed in 1955. "Lord Baltimore" is itself a near-sterile hybrid, its ancestry including *Hibiscus militaris, Hibiscus coccineus, Hibiscus moscheutos,* and *Hibiscus palustris.* Because of the shy seeding habit of "Lord Baltimore" (a flower-to-seedpod ratio of approximately 250 to 1), no attempt was made to keep the crosses exclusive. As far as possible, pollen was manually delivered from selected pink-flowered hibiscus plants; but there was no exclusion of the serendipitous bee. Selections were continuously made from the seedlings so derived.

The new plant produced its first flower in the summer of 1972, and because of the beautiful coloring and substance of its blooms, together with its attractive habit, it was selected for reproduction and test. Asexual propagation of this new plant by cuttings and division was carried on at College Park, Md., and observation of the progeny of the original plant has demonstrated that this new variety has fulfilled the objective and that its distinctive characteristics are firmly fixed and hold true from generation to generation.

DESCRIPTION OF THE DRAWINGS

This new variety of hibiscus plant is illustrated by the accompanying full color photographic drawings which show, first, the fully opened flower, and second, some typical leaves of this variety, the colors shown being as true as can be reasonably done by conventional photographic procedures.

DESCRIPTION OF THE NEW PLANT

The following is a detailed description of the new variety, color terminology being in accordance with the *Royal Horticultural Society Colour Chart,* except where otherwise indicated to have ordinary dictionary significance.

THE PLANT

Type: Tender; herbaceous perennial.
Classification: Hybrid variety of hibiscus.
Origin: Seedling.
Parentage:
*Seed parent.*—"Lord Baltimore."
*Pollen parent.*—Unknown (selected from progeny of "Lord Baltimore" open-pollinated (but with most alien pollen obtained from selected pink-flowered hibiscus and manually delivered)).
Propagation: Holds its distinguishing characteristics through succeeding propagations by cuttings and division.
Form: Bushy annual growth from perennial roots.
Habit: Upright and much branched.
Growth: Vigorous and moderately free.
Leaves: Moderately abundant; finely cut; decorative.
*Margins.*—Length 2 to 7 inches; irregularly serrate.
*Color.*—Medium green. Underside of leaves — light green. New leaves — light green and shiny.
*Petiole.*—Length 1 to 4 inches. Lenticels — none.
*Form.*—Mostly three- to five-parted; palmately lobed.
*Stipules.*—None.
Stem: Light green, with fugitive slightly pinkish cast.
Height: Medium — 4 to 5 feet.

THE FLOWER

Date described: Sept. 2, 1977.

Blooming habit: Continuous and free blooming.
Petals: Length — 3 to 4 inches.
Diameter: 6 to 8 inches.
Shape: Widely flared bell, with petals overlapping and ruffled.

Stamen tube: Color — Pink (approximately RHS 62D), shading to red (approximately RHS 45D) in filament area.

Filaments: Color — Pink (approximately RHS 62D).

Stamens: Numerous.

Stigma: Color — Pink (approximately RHS 62D), with fine setae providing overtones of red (RHS 45D).

Style: Color — Pink (approximately RHS 62D).

Base of pistil or very center of throat: Color — Pink (approximately RHS 62D).

Pollen: Color — Grey (approximately RHS 201D).

Shape of flower: Round; widely flared bell.

Petalage: Single — five petals arranged regularly, overlapping and ruffled.

Shape of Petals: Broadly obovate (almost reniform), recurved at base to form slight green star of revealed calyx.

Aspect of flower:

*Central one-third.*—Satiny;

*Outer two-thirds.*—Velvety.

Texture: Leathery and moderately thick.

Color of flower:

*Inside.*—Large satiny red center (RHS 45A, shading into RHS 45B) comprising about one-third of each petal, with prominent reddish veins (approximately RHS 45D) extending into the outer pink area. The general effect of the outer area is of a velvety orchid pink (approximately RHS 62C grading into RHS 62D), with fine reticulations of slightly darker hue. From a distance, the total effect is of a glowing guardsman-red sunburst in the middle of a light pink cloud. It should be noted that the red center is much larger than the usual hibiscus "eye."

*Outside.*—Light red-and-pink pinwheel effect (approximately one-third of each petal longitudinally is heavily veined with red (RHS 45D) against a background of pink (approximately RHS 62D)).

Calyx: Five-toothed, light yellowish green.

Bractlets: Medium green.

Flowers: Numerous; elegant in appearance; individual flower lasting 1 day.

Blooming period: July to frost. When all buds on an individual branch have bloomed, new growth with new buds develops. Occasionally, frost has caught some of the plants in their *third* stage of blooming. From the onset of the blooming period, the plant is seldom without flowers.

Peduncle: Length — 3 to 5 inches; medium thickness; stiff.

Stipules: None.

I claim:

1. A new and distinctive cultivar of hibiscus substantially as herein shown and described, a glowing pink-and-red bicolor of elegant form and substance, a plant of great landscape value, blooming profusely from midsummer to frost.

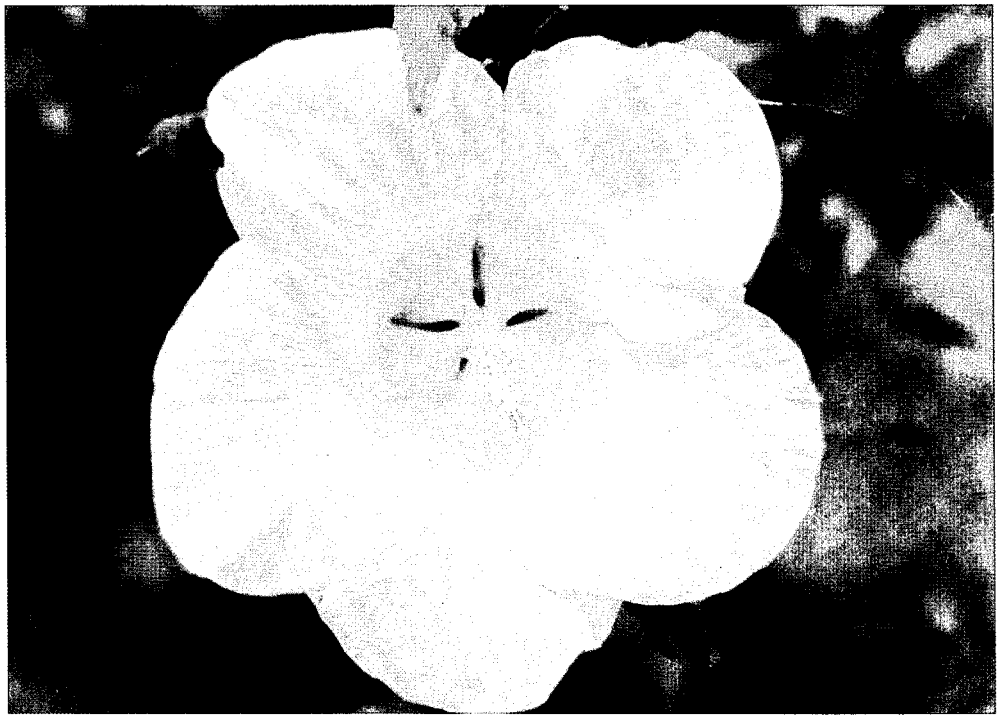
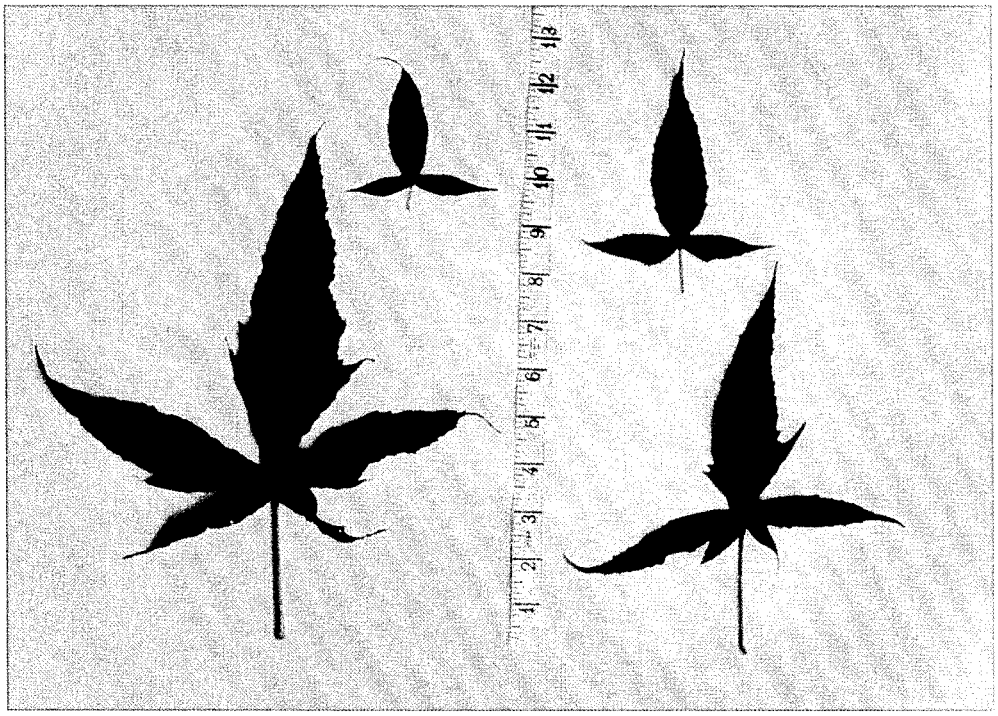

* * * * *